United States Patent [19]
Greer

[11] Patent Number: 4,641,643
[45] Date of Patent: Feb. 10, 1987

[54] RESEALING SKIN BANDAGE

[76] Inventor: Leland H. Greer, 530 E. 12th St., Oakland, Calif. 94606

[21] Appl. No.: 856,312

[22] Filed: Apr. 28, 1986

[51] Int. Cl.⁴ .............................................. A61L 15/00
[52] U.S. Cl. .................................................. 128/156
[58] Field of Search ............... 128/156, 260, 268, 158, 128/287, 296

[56] References Cited

U.S. PATENT DOCUMENTS

| | | | |
|---|---|---|---|
| 679,993 | 8/1901 | Taggart et al. | |
| 2,233,209 | 2/1941 | Herzog | 128/156 |
| 2,273,873 | 2/1942 | Klein | 128/156 |
| 2,303,131 | 11/1942 | Morgan | 128/156 X |
| 2,561,849 | 7/1951 | Collignon | 128/156 |
| 2,632,443 | 3/1953 | Lesher | 128/156 |
| 3,042,037 | 7/1962 | Scales et al. | 128/156 |
| 3,616,156 | 10/1971 | Scholl | 161/121 |

*Primary Examiner*—Gregory F. McNeill
*Attorney, Agent, or Firm*—Bielen and Peterson

[57] ABSTRACT

A resealing skin bandage utilizing a flexible body having first and second opposite surfaces. The flexible body includes an opening through its central portion which extends from the first surface to the second surface. The flexible body is removably fixed to the skin at the first surface. A flexible layer of water repellant material overlies the flexible body and is bonded to the second surface of the body. A cover is removably held to the flexible layer.

9 Claims, 3 Drawing Figures

RESEALING SKIN BANDAGE

BACKGROUND OF THE INVENTION

The present invention relates to a novel resealing skin bandage.

Many kinds of wounds such as fitulas or ulcers (decubitus) are normally bandaged using the prior art gauze and adhesive tape combination. Gauze is normally used to absorb liquid secretions and excrements from the wounds. For example, fecal matter must be emptied one to four times a day from an internal pouch formed by the Koch procedure.

Unfortunately, removal of the conventional prior art bandage often tears the skin, removes hair resulting in follicle infections or rashes. This undesirable affect is especially acute with wounds that must be examined a multiplicity of times per day. Bandages such as those shown in U.S. Pat. Nos. 679,993 and 3,616,156 have been devised which employ adhesive which is designed to stay on the skin for a relatively long period of time. However, these bandages are not suitable for wounds having matter which oozes therefrom.

U.S. Pats. Nos. 2,632,443 and 3,042,037 describe wounds dressing that are of the type requiring replacement after saturation by fluids from the wound.

A bandage which may be placed on a wound and is resealable without removal of the same would be a great advance in the medical field.

SUMMARY OF THE INVENTION

In accordance with the present invention a novel resealable skin bandage is provided. The bandage of the present invention utilizes a flexible body which may be resilient. The flexible body includes a first surface and a second opposite surface. An opening is provided through the flexible body between surfaces. Means is also included for removably fastening the flexible body to the skin with the first surface of the flexible body in contact with the skin.

The bandage of the present invention also includes a flexible layer of water repellent material which has an opening through the same. Means is employed for bonding the flexible layer to the second surface of the flexible body such that the opening through the flexible layer aligns with at least a portion of the opening through the flexible body.

The bandage is further constructed with a cover and means for removably holding the cover to the flexible layer of water repellant material. The cover may be constructed of water repellent material and be opaque, translucent, or transparent. Thus, in certain cases the wound may be observed through the cover without removal of the same. The cover may also be formed to hingedly connect to the flexible layer. In certin embodiments, the flexible layer and the cover may be contiguous. The cover may further include a tab which extends beyond the periphery of the flexible body and is thus readily available to the user when the cover is removably held to the flexible layer.

Means for removably holding the cover to the flexible layer may comprise the utilization of a tape having a first adhesive layer which contacts the flexible layer and a second adhesive layer which contacts the cover. The first adhesive layer would be mroe readily separable from the flexible layer than from the tape when the cover is in place on the flexible layer. Also, the second layer of the tape would bond to the cover more strongly than the first adhesive layer would bond to the flexible layer. Consequently, the cover with tape attached would be able to seal itself against the flexible layer and be removed therefrom without the tape separating from the cover.

It may be apparent that a novel and useful resealable bandage has been described.

It is therefore an object of the present invention to provide a resealable skin bandage which possess a portion which affixes to the skin and is not required to be removed therefrom when a wound covered by the bandage is cleaned and/or drained at periodic intervals.

Another object of the present invention is to provide a sealable skin bandage which eliminates irritation to the skin caused by prior art replaceable bandages.

Yet another object of the present invention is to provide a resealable skin bandage which includes a removable portion that does not contact the skin and permits repeated access to the wound being covered by the bandage.

Still another object of the present invention is to provide a resealable skin bandage which includes a cover that is hingedly attached to a base such that the cover removed from the base is not lost or damaged and may be reused to cover the base portion of the bandage.

The invention other objects and advantages especially as concerns particular characteristics and features thereof which will become apparent as the specification continues.

Figure 3:
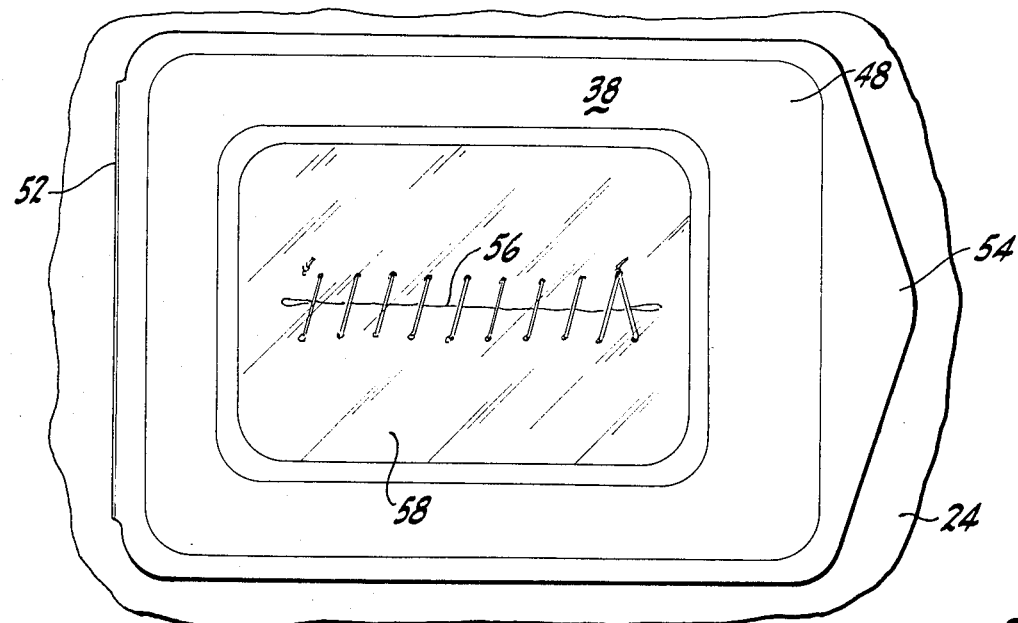
FIG. 3 is a top plan view of the bandage of the present invention in place on a skin surface.

For a better understanding of the invention reference is made to the following detailed description of the preferred embodiments thereof which should be referenced to the hereinabove described drawings.

DESCRIPTION OF THE PREFERRED EMBODIMENTS

Various aspects of the present invention will evolve from the following detailed description of the preferred embodiments which should be taken in conjunction with the hereinabove described drawings.

The invention as a whole is shown in the drawings by reference character 10. The bandage 10 includes as one of its elements a flexible body 12 having a first surface 14 and a second surface 16. Flexible body 12 may take the form of a piece of poly-urethane open-cell foam such that body 12 exhibits flexibility and resiliency. Thus, body 12 is suitable for non-flat portions of the body such as the palm of the hand, the shoulder, and the like. Adhesive layers 18 and 20 are fixed to first and second surfaces 14 and 16, respectively. Adhesive layers 18 and 20 may be composed of any medical grade E.K.G. adhesive. A plastic layer 22 is easily removable from adhesive layer 18 to expose adhesive layer 18 for eventual adhesion to a skin surface 24, FIG. 3. Plastic layer 22 is disposable in this regard. Flexible body 12 includes an opening 26 through the same between first and second surfaces 14 and 16. Plastic layer 22 would enclose the bottom portion of opening 24 before bandage is used, such as during shipping and/or storage. Thus, adhesive 18 serves as means 28 for removably fastening first surface 14 of flexible body 12 to skin surface 24.

A flexible layer 30 overlays adhesive layer 20 which constitutes means 22 for bonding flexible layer 30 to second surface 16 of body 12. Flexible layer 30 is constructed of water repellent, non-absorbant material such as polyethylene. Upper surface 34 of flexible layer 30 is smooth and easily cleaned of exudate. Flexible layer 30 includes an opening 36 through the same such that opening 36 aligns with at least a portion of opening 26 of body 12 when flexible layer 30 is bonded to body 12.

A cover 38 is intended for overlaying openings 26 and 36 of body 12 and layer 30 respectively. Means 40 removably holds cover 38 to flexible layer 30. Means 40 may take the form of a plastic tape 42 having a lower first surface 46 and an opposite upper surface 46. Adhesive layer 48 bonds second upper surface 46 to cover 38. Adhesive layer 50, on the other hand, removably holds first surface 44 of tape 42 to the smooth upper surface of flexible layer 30.

Flexible layer 30 and cover 38 are depicted as being contiguous and being constructed of the same material. Consequently, cover 38 and flexible layer 34 may include hinge 52. Cover 38 also includes a tab portion 54 to aid the user in lifting cover 38 from flexible layer 30. Cover 38 may be constructed of opaque, translucent, or transparent material. In FIG. 3, cover 38 is depicted as being relatively translucent such that adhesive layer 48 and wound 56 on skin surface 24 is shown with cover 38 in sealing engagement with adhesive layer 48.

Figure 2:
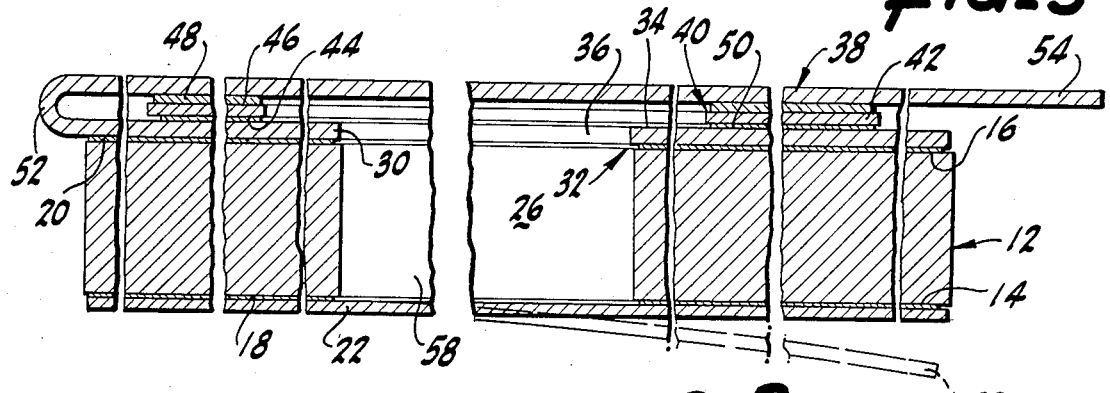
FIG. 2 is a broken sectional view taken along line 2—2 of FIG. 1.
Figure 1:
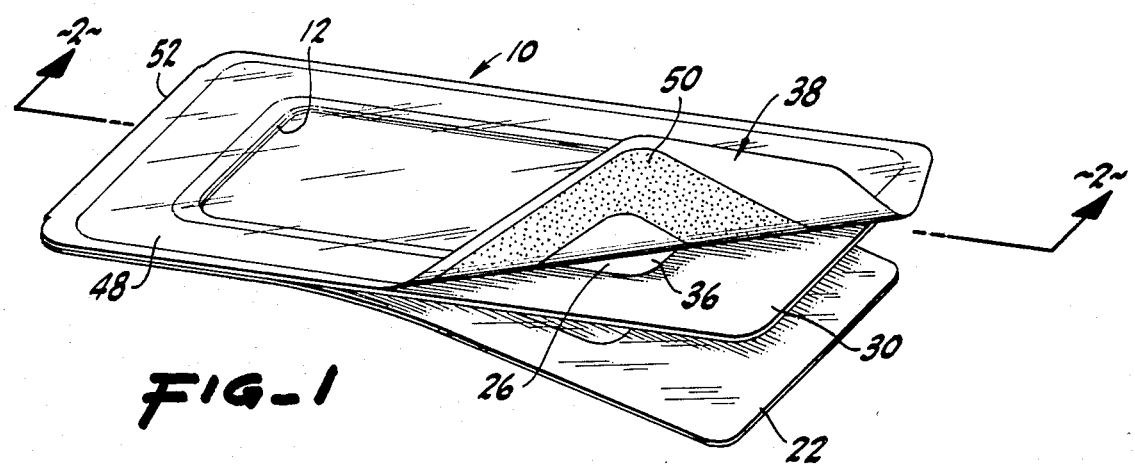
FIG. 1 is a top right side perspective view of the bandage of the present invention with portions partly peeled apart.

In operation, the user peels and generally discards, plastic layer 22 from the adhesive layer 18 on first surface 14 of body 12, shown as partially removed in FIGS. 1 and 2. Such removal exposes openings 26 and 36 for placement around wound 56. Adhesive layer 18 produces a seal on skin surface 24 around wound 56 to prevent seepage of exudate from the space around wound 56. It should be noted that plastic layer 22 and cover 38 in the sealed position form a chamber 58 which may be easily sterilized before use of bandage 10. Cover 38 is easily removable from flexible layer 30 to gain access to chamber 58 when bandage 10 is affixed to skin surface 24. Thus, wound 56 may be sterilized, cleaned, drained, or otherwise treated without removal of body 12 from skin surface 24. In certain cases, absorbent material such as cotton, gauze, and the like may be placed within chamber 58. After treatment of wound 56, cover 38 may be resealed on flexible layer 30. This procedure may be repeated numerous times without removal of flexible body 12 from skin surface 24. It should be noted, that means 40 for removably holding cover 38 to flexible layer 30 generates a weaker adhesion then means 28 for holding first surface 14 of body 12 to skin surface 24. As a result, when tab 54 is grasped and cover 38 is lifted from flexible layer 30, flexible body 12 remains in place on skin surface 24.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A resealing skin bandage comprising:
   a. a flexible body having a first surface and a second opposite surface said flexible body including an opening therethrough from said first surface to said second surface;
   b. means for removably fastening said flexible body first surface to the skin;
   c. a flexible layer of water repellent material said flexible layer having an opening therethrough;
   d. means for bonding said flexible layer to said second surface of said flexibility body, said opening through said flexible layer aligning with at least a portion of said opening through said flexible body;
   e. A cover intended to overlay said at least partially aligned openings through said flexible body and said flexible layer; and
   f. means for removably holding said cover to said flexible layer of water repellant material.

2. The bandage of claim 1 in which said flexible layer is hingedly connected to said cover.

3. The bandage of claim 2 in which said flexible layer is continuous with said cover.

4. The bandage of claim 3 in which said cover includes a translucent portion which aligns with at least a portion of said opening through said flexible body.

5. The bandage of claim 1 in which said flexible body is also a resilient body.

6. The bandage of claim 1 in which said cover further includes a tab which extends beyond the periphery of said flexible body.

7. The bandage of claim 1 in which said means for removably holding said cover to said flexible layer of water repellant material comprises a tape having a first adhesive layer for contacting said flexible layer and a second adhesive layer for contacting said cover, said first adhesive layer being more readily separable from said flexible layer than from said tape.

8. The bandage of claim 7 in which said second adhesive layer of said tape bonds to said cover more strongly than said first adhesive layer bond to said flexible layer.

9. The bandage of claim 8 in which said means for removably fastening said flexible body first surface to the skin holds said flexible body to the skin when said cover is removed from said flexible layer.

* * * * *